United States Patent
Landvik et al.

(10) Patent No.: US 9,765,409 B2
(45) Date of Patent: Sep. 19, 2017

(54) POLYPEPTIDES HAVING DEXTRANASE ACTIVITY AND POLYNUCLEOTIDES ENCODING SAME

(71) Applicant: NOVOZYMES A/S, Bagsvaerd (DK)

(72) Inventors: Sara Landvik, Copenhagen (DK); Lorena G. Palmen, Malmo (SE); Thiago O. Basso, Curitiba (BR); Eduardo Alberto Borges Da Silva, Sao Jose (BR)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/782,162

(22) PCT Filed: Apr. 4, 2014

(86) PCT No.: PCT/EP2014/056829
§ 371 (c)(1),
(2) Date: Oct. 2, 2015

(87) PCT Pub. No.: WO2014/161987
PCT Pub. Date: Oct. 9, 2014

(65) Prior Publication Data
US 2016/0053336 A1    Feb. 25, 2016

(30) Foreign Application Priority Data
Apr. 5, 2013   (EP) .................... 13162491

(51) Int. Cl.
*C13B 20/00*    (2011.01)
*C12N 9/46*    (2006.01)
*C12N 9/96*    (2006.01)

(52) U.S. Cl.
CPC .......... *C13B 20/002* (2013.01); *C12N 9/2454* (2013.01); *C12N 9/96* (2013.01); *C12Y 302/01011* (2013.01)

(58) Field of Classification Search
None
See application file for complete search history.

(56) References Cited

FOREIGN PATENT DOCUMENTS

CN    102703480 A    10/2012
WO    2005/073368 A1    8/2005

OTHER PUBLICATIONS

Covacevich et al, 1977, In Proc XVI ISSCT Cong 2493-2508.
Donavan, 1993, Proc Sugar Ind technol 52, 117-130.
Cuddihy et al, 1998, Midland Research Laboratories, Inc.
Eggleston et al, 2009, Sugar Tech 11 (2), 135-141.
Imrie et al, 1972, Sugar Tech Reviews 1, 291-361.
Geronimos et al, 1978, 45th Conference, 119-126.
Kim et al, 2004, Food Scie Biotechnol 13, 248-252.
Ravno et al, 2006, Intl Sugar J 108, 255-269.
Vane, 1981, Proc Sugar Ind Technol 40, 95-102.
Singleton et al, 2001, Intl Sugar J 103(1230), 251-254.
Rerngsamran et al, 2008, Uniport Access No. B2MW82.
Haynes et al., Proceedings of the 2004 Sugar Processing Research Conference, pp. 138-146 (Sep. 2004).

*Primary Examiner* — David J Steadman
(74) *Attorney, Agent, or Firm* — Elias J. Lambiris

(57) ABSTRACT

The present invention relates to isolated polypeptides having dextranaseactivity, and polynucleotides encoding the polypeptides. The invention also relates to nucleic acid constructs, vectors, and host cells comprising the polynucleotides as well as methods of producing and using the polypeptides.

20 Claims, 6 Drawing Sheets

SEQUENCE LISTING

```
<160> NUMBER OF SEQ ID NOS: 4

<210> SEQ ID NO 1
<211> LENGTH: 1785
<212> TYPE: DNA
<213> ORGANISM: Acrophialophora fusispora

<400> SEQUENCE: 1
atgttttctg ttcttctggg ctggctgctg ttccagccgg cggttggaac ttgcattcca      60
ccacgcaacg gcaaccacac ggtgtgcaac aaccagctgt gcacctggtg gcacgacaac     120
ggcgagatca acacaaacag catggtgcag ctgggcaatg ttcgccagtc gcgcaagtac     180
ttggtgcaag tgagcatcgc cggcgctgac aacttctacg actcgttcgc ctacgagtcg     240
atcccccgca acgccgtgg ccgcatctac tcgcccctggg acgcccctga cagcaacacc     300
ctggcgtcag acgtggatga tggcatcacc attgagccca acgtcggcat caatatggcc     360
tggtcccagt tcgagtactc caccggcgtt gaagtcaaga tccgcacact cgacggctca     420
tctctccctg gcccgtccgg ggtcaagatc cgcccgacgg ccatcagcta cggcattcgc     480
tcatctggcg acggcggtat cattatccac gtgccgcacg acccgaacgg ccggaggttc     540
tctgtcgagt tcgacaatga tttgtacaca taccgctccg acggcttgca ctacgtcccc     600
tcgggcggct ccgtcgtggg cgtggaaccg aaaaatgctc tgcttatctt cgcaagcccc     660
ttcttgcctg ccgacatggt cccgcgcatc gacgggcctg acaccaaagt tatgactcct     720
gggccgatca atcaaggcga ctggggctcg tccagtatcc tgtacttccc tcctggggta     780
tattggatga actccaaccc gcagggccag actcctaaga ttggcgaaaa ccacatccgg     840
cttcacccca acacgtactg ggtgtacttg gcgcctggtg cgtacgtcaa gggcgcgatt     900
gagtactcga ccaagtcgaa cttctacgca accggccacg gcgtcttgtc cggcgagcac     960
tacgtctacc aggcaaaccc ggcgacctac taccaggccc tgaagagcga cgccaccagc    1020
ttgcgcatgt gggggcacaa caacctcggt ggcggccaga catggttctg ccaaggcccg    1080
accatcaacg cgccgccgtt caacacgatg gatttccacg gaagctccga catcacgacc    1140
cgcatctcgg attacaagca agtgggcgcc tttttcttcc agaccgacgg gcctcaaatg    1200
```

```
tatcccaaca gccaggtcca cgacgtcttc taccacgtca atgacgacgc catcaagacc   1260
tactactcgg gcgtgacggt gacgcgggcg accatctgga agggccacaa cgaccccatc   1320
gtccagatgg ggtgggatac gcgcgatgtt tcaggcgtca ctctgcagga catccacgtc   1380
atccacaccc gctacatcaa gtccgagaca tatgtgccgt cggccatcat cggggcgtcg   1440
cccttctaca tgtccggacg ctcagtcgac ccgtccaaga ccatcagcat gaccatctcc   1500
ggcctggtgt gcgaggggct gtgtccggcg ctgatgcgca taacgccgct tcaaaactac   1560
cgcgacttcc gtatcgagaa cgttgcgttc cccgacgggc tgcagaccaa cagcatcggc   1620
acgggcagaa gtattgtccc tgcctcctcc ggtctcaggt tcggcgtgac catctcaaac   1680
tggactgtgg gcggccatcg ggtgacgatg agcaacttcc agtctgattc gcttgggcag   1740
cttgatatcg atgtttctta ctgggggcag tgggctatta attga                  1785
```

<210> SEQ ID NO 2
<211> LENGTH: 594
<212> TYPE: PRT
<213> ORGANISM: Acrophialophora fusispora

<400> SEQUENCE: 2

```
Met Phe Ser Val Leu Leu Gly Trp Leu Leu Phe Gln Pro Ala Val Gly
1               5                   10                  15

Thr Cys Ile Pro Pro Arg Asn Gly Asn His Thr Val Cys Asn Asn Gln
            20                  25                  30

Leu Cys Thr Trp Trp His Asp Asn Gly Glu Ile Asn Thr Asn Ser Met
        35                  40                  45

Val Gln Leu Gly Asn Val Arg Gln Ser Arg Lys Tyr Leu Val Gln Val
    50                  55                  60

Ser Ile Ala Gly Ala Asp Asn Phe Tyr Asp Ser Phe Ala Tyr Glu Ser
65                  70                  75                  80

Ile Pro Arg Asn Gly Arg Gly Arg Ile Tyr Ser Pro Trp Asp Ala Pro
                85                  90                  95

Asp Ser Asn Thr Leu Ala Ser Asp Val Asp Asp Gly Ile Thr Ile Glu
            100                 105                 110

Pro Asn Val Gly Ile Asn Met Ala Trp Ser Gln Phe Glu Tyr Ser Thr
        115                 120                 125

Gly Val Glu Val Lys Ile Arg Thr Leu Asp Gly Ser Ser Leu Pro Gly
    130                 135                 140

Pro Ser Gly Val Lys Ile Arg Pro Thr Ala Ile Ser Tyr Gly Ile Arg
145                 150                 155                 160

Ser Ser Gly Asp Gly Gly Ile Ile Ile His Val Pro His Asp Pro Asn
                165                 170                 175

Gly Arg Arg Phe Ser Val Glu Phe Asp Asn Asp Leu Tyr Thr Tyr Arg
            180                 185                 190

Ser Asp Gly Leu His Tyr Val Pro Ser Gly Gly Ser Val Val Gly Val
        195                 200                 205

Glu Pro Lys Asn Ala Leu Leu Ile Phe Ala Ser Pro Phe Leu Pro Ala
    210                 215                 220

Asp Met Val Pro Arg Ile Asp Gly Pro Asp Thr Lys Val Met Thr Pro
225                 230                 235                 240

Gly Pro Ile Asn Gln Gly Asp Trp Gly Ser Ser Ile Leu Tyr Phe
                245                 250                 255

Pro Pro Gly Val Tyr Trp Met Asn Ser Asn Pro Gln Gly Gln Thr Pro
            260                 265                 270
```

Lys Ile Gly Glu Asn His Ile Arg Leu His Pro Asn Thr Tyr Trp Val
        275                 280                 285

Tyr Leu Ala Pro Gly Ala Tyr Val Lys Gly Ala Ile Glu Tyr Ser Thr
        290                 295                 300

Lys Ser Asn Phe Tyr Ala Thr Gly His Gly Val Leu Ser Gly Glu His
305                 310                 315                 320

Tyr Val Tyr Gln Ala Asn Pro Ala Thr Tyr Gln Ala Leu Lys Ser
                325                 330                 335

Asp Ala Thr Ser Leu Arg Met Trp Gly His Asn Asn Leu Gly Gly
                340                 345                 350

Gln Thr Trp Phe Cys Gln Gly Pro Thr Ile Asn Ala Pro Pro Phe Asn
                355                 360                 365

Thr Met Asp Phe His Gly Ser Ser Asp Ile Thr Thr Arg Ile Ser Asp
        370                 375                 380

Tyr Lys Gln Val Gly Ala Phe Phe Phe Gln Thr Asp Gly Pro Gln Met
385                 390                 395                 400

Tyr Pro Asn Ser Gln Val His Asp Val Phe Tyr His Val Asn Asp Asp
                405                 410                 415

Ala Ile Lys Thr Tyr Tyr Ser Gly Val Thr Val Thr Arg Ala Thr Ile
                420                 425                 430

Trp Lys Gly His Asn Asp Pro Ile Val Gln Met Gly Trp Asp Thr Arg
                435                 440                 445

Asp Val Ser Gly Val Thr Leu Gln Asp Ile His Val Ile His Thr Arg
        450                 455                 460

Tyr Ile Lys Ser Glu Thr Tyr Val Pro Ser Ala Ile Ile Gly Ala Ser
465                 470                 475                 480

Pro Phe Tyr Met Ser Gly Arg Ser Val Asp Pro Ser Lys Thr Ile Ser
                485                 490                 495

Met Thr Ile Ser Gly Leu Val Cys Glu Gly Leu Cys Pro Ala Leu Met
                500                 505                 510

Arg Ile Thr Pro Leu Gln Asn Tyr Arg Asp Phe Arg Ile Glu Asn Val
                515                 520                 525

Ala Phe Pro Asp Gly Leu Gln Thr Asn Ser Ile Gly Thr Gly Arg Ser
                530                 535                 540

Ile Val Pro Ala Ser Ser Gly Leu Arg Phe Gly Val Thr Ile Ser Asn
545                 550                 555                 560

Trp Thr Val Gly Gly His Arg Val Thr Met Ser Asn Phe Gln Ser Asp
                565                 570                 575

Ser Leu Gly Gln Leu Asp Ile Asp Val Ser Tyr Trp Gly Gln Trp Ala
                580                 585                 590

Ile Asn

<210> SEQ ID NO 3
<211> LENGTH: 44
<212> TYPE: DNA
<213> ORGANISM: Artificial
<220> FEATURE:
<223> OTHER INFORMATION: PCR primer

<400> SEQUENCE: 3
acacaactgg ggatccacca tgttttctgt tcttctgggc tggc        44

<210> SEQ ID NO 4
<211> LENGTH: 41
<212> TYPE: DNA

```
<213> ORGANISM: Artificial
<220> FEATURE:
<223> OTHER INFORMATION: PCR primer

<400> SEQUENCE: 4
agatctcgag aagcttatca attaatagcc cactgccccc a                          41
```

POLYPEPTIDES HAVING DEXTRANASE ACTIVITY AND POLYNUCLEOTIDES ENCODING SAME

CROSS-REFERENCE TO RELATED APPLICATIONS

This application is a 35 U.S.C. 371 national application of PCT/EP2014/056829 filed Apr. 4, 2014, which claims priority or the benefit under 35 U.S.C. 119 of EP application no. 13162491.8 filed Apr. 5, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having dextranase activity, and polynucleotides encoding the polypeptides. The invention also relates to nucleic acid constructs, vectors, and host cells comprising the polynucleotides as well as methods of producing and using the polypeptides.

Description of the Related Art

Dextran (polysaccharide with high molecular weight and predominantly straight-chained glucose polymer with a majority of alpha-1-6 glucosidic linkages) is highly undesirable impurity causing severe processing problems in sugarcane mills and sugar beet mills as well as sugar refineries. The effects of the presence of dextran on sugar mill flow are numerous and varied (Imrie F K E, Tilbury R H. (1972). Polysaccharides in sugar cane and its products. Sugar Technology Reviews 1972; 1:291-361; Rauh J S, Cuddihy J A, Opelka M J. (1999). Analyzing Dextran in the Sugar Industry: A Review of Dextran in the Factory and a New Analytical Technique. 30th Biennial Meeting, American Society of Sugar Beet Technologists, 1999, Orlando, Fla., USA.; Eggleston, G, Monge A, Montes B, Stewart D (2009), Application of dextranases in sugarcane factory: Overcoming practical, Sugar Tech (2009) 11(2): 135-141), bringing about significant losses to the sugar industries: the raw sugar industry and the refined sugar industry. Dextran is formed irreversibly from the sucrose contained in the raw materials (Cuddihy J A, Rauh J S, Porro M E. (1998). Improving sugar recovery with sugar process chemicals. Midland Research Laboratories, Inc. 1998). The most significant impact of the dextran contamination is on the viscosity of sugar processing streams. Dextran in raw juices causes poor clarification since it acts as a protective colloid inhibiting the coagulation phase in the decanter (Ravno, A. B., and B. B. Purchase. 2006. Dealing with dextran in the South African sugar industry. International Sugar Journal 108:255-269). As a result, more color and ash are expected in the sugar made from such juice with fine suspended matter. Sugar refineries can face large challenges on the filtration rates leading to reduced throughput due to the presence of this suspended matter (Donavan, M, 1993, Raw sugar quality. The effect on the refiner. Proc. Sugar. Ind. Technol., 52, 117-130). The increased viscosity caused by the dextran in sugar processing streams interferes negatively on heat transfers rates, increases scale deposits on evaporators/heaters, lower molasses exhaustion and lower purging efficiency in centrifuges (Geronimos, G. L and P. F. Greenfield (1978). Viscosity increases in concentrated sugar solutions and molasses due to dextrans. In proceedings of the Queesland Society of Sugar Cane Technologist, 45$^{th}$ Conference, Quaeesland, Australia, 119-126; Singleton, V., Horn, J., Bucke, C. and Adlard, M. (2001): A new polarimetric method for the analysis of dextran and sucrose. *International Sugar Journal*, 103(1230), 251-254; Kim, D and Day D. F, (2004), Determination of dextran in raw sugar process streams, Food Science and Biotechnology, 13:248-252). The presence of dextran also influences the rate of crystallization and causes elongation of sugars crystals (Covacevich M T, Richards G N and G Stokie (1977). Studies on the effect of dextran structure on cane sugar crystal elongation and methods of analysis. In Proceedings of the XVI ISSCT Congress, Sao Paulo, S P, Brazil, 2493-2508) with severe drawbacks for the end chain factories of sugar (Vane G. W. (1981) The effect of dextran on the distortion of hard candy. Proc. Sugar Ind. Technol., 40, 95-102; Haynes, L Zhou L and Hopkins W (2004). Dextran in refined sugar: impact on hard candy processing. Proc. Sugar Proc Res Inst: 138-146)). Thus it can be concluded that the benefits resulting in removal of dextran include viscosity decrease leading to increased sugar recovery and also to improve sugar quality. In particular it is the high molecular mass dextran (>10$^6$ g/gmol) that has an impact on viscosity and handling properties of massecuites, and thus this is the type of dextran that needs to be targeted by the dextranase.

Dextranase is often added before the last evaporator when dextran levels are high, or in juice tanks.

Several commercial Dextranase products are available, e.g., Dextranase Plus L (Novozymes NS) which is a dextranase from *Chaetomium erraticum*.

There is a need in the art for improved dextranase enzymes useful for reducing dextran content in sugar solutions in sugarcane mills, sugar beet mills as well as sugar refineries.

SWISSPROT:B2MW82 discloses a dextranase from *Talaromyces pinophilus*.

The present invention provides polypeptides having dextranase activity and polynucleotides encoding the polypeptides.

SUMMARY OF THE INVENTION

The present invention relates to an isolated polypeptide having dextranase activity, selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a polypeptide encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i);

(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;

(d) a variant of the mature polypeptide of SEQ ID NO: 2 comprising a substitution, deletion, and/or insertion at one or more positions; and (e) a fragment of the polypeptide of (a), (b), (c), or (d) that has dextranase activity.

In a further aspect the present invention relates to a composition comprising the polypeptide of the invention and a stabilizer.

In a still further aspect the invention relates to a use of the dextranase of the invention, for reducing viscosity in a sugar solution.

In another further aspect the invention relates to a method for reducing viscosity in a sugar solution comprising contacting the sugar solution with a dextranase according to the invention.

The present invention also relates to isolated polynucleotides encoding the polypeptides of the present invention; nucleic acid constructs; recombinant expression vectors; recombinant host cells comprising the polynucleotides; compositions comprising the polypeptide of the invention; and methods of producing the polypeptides.

DEFINITIONS

Figure 1:
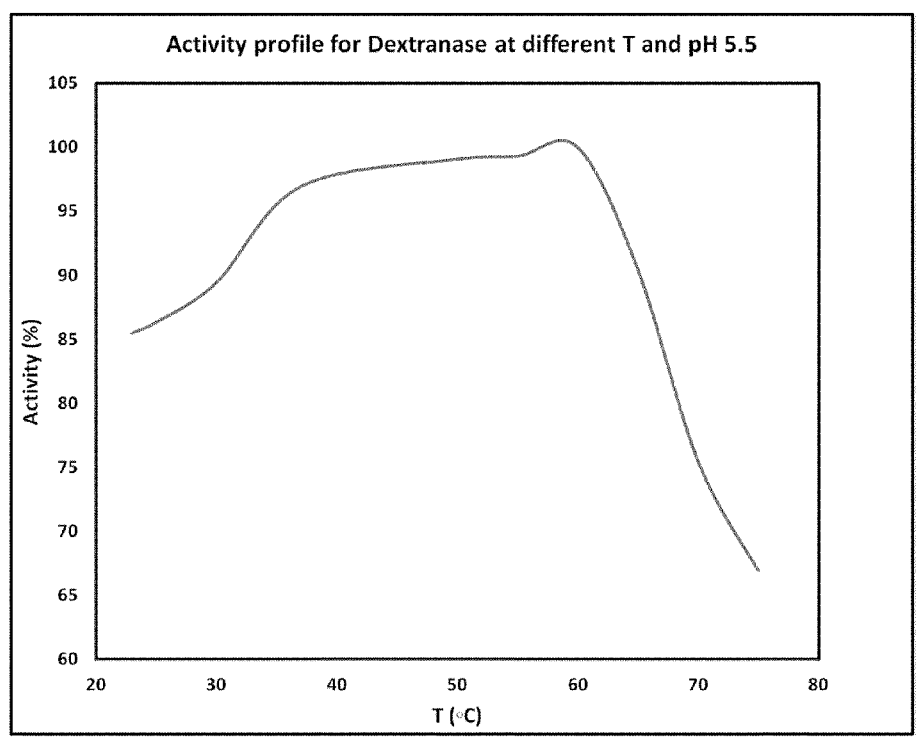
FIG. 1 shows the temperature activity profile for the dextranase of the invention ($T_{max}$=62° C., pH=5.5).

Dextranase: The term "dextranase" means a glycoside hydrolase family 49 activity (EC 3.2.1.11) that catalyzes the hydrolysis of the glycosidic bond between two or more carbohydrates, or between a carbohydrate and a noncarbohydrate moity. The family GH49 dextranases hydrolyses alpha-1,6-glycosidic bonds in dextran polymers. For purposes of the present invention, dextranase activity is determined according to the procedure described in the Examples. In one aspect, the polypeptides of the present invention have at least 20%, e.g., at least 40%, at least 50%, at least 60%, at least 70%, at least 80%, at least 90%, at least 95%, or at least 100% of the dextranase activity of the mature polypeptide of SEQ ID NO: 2. Dextranase activity can be determined according to the assay described in the examples (e.g. example 2).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has dextranase activity. In one aspect, a fragment contains at least 570 amino acid residues (e.g., amino acids 25 to 594 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 17 to 594 of SEQ ID NO: 2 and amino acids 1 to 16 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having dextranase activity. In one aspect, the mature polypeptide coding sequence is nucleotides 49 to 1782 of SEQ ID NO: 1 and nucleotides 1 to 48 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having dextranase activity. In one embodiment the subsequence corresponds to the polynucleotide encoding the catalytic domain. In one aspect, a subsequence contains at least 1710 nucleotides (e.g., nucleotides 73 to 1782 of SEQ ID NO: 1).

Variant: The term "variant" means a polypeptide having dextranase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides having Dextranase Activity

In an embodiment, the present invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, which have dextranase activity. In one aspect, the polypeptides differ by no more than 10 amino acids, e.g., 1, 2, 3, 4, 5, 6, 7, 8, or 9, from the mature polypeptide of SEQ ID NO: 2.

In a particular embodiment the invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the dextranase activity of the mature polypeptide of SEQ ID NO: 2.

In a particular embodiment the invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 80% of the dextranase activity of the mature polypeptide of SEQ ID NO: 2.

In a particular embodiment the invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 90% of the dextranase activity of the mature polypeptide of SEQ ID NO: 2.

In a particular embodiment the invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 95% of the dextranase activity of the mature polypeptide of SEQ ID NO: 2.

In a particular embodiment the invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 100% of the dextranase activity of the mature polypeptide of SEQ ID NO: 2.

A polypeptide of the present invention preferably comprises or consists of the amino acid sequence of SEQ ID NO: 2 or an allelic variant thereof; or is a fragment thereof having dextranase activity. In another aspect, the polypeptide comprises or consists of the mature polypeptide of SEQ ID NO: 2. In another aspect, the polypeptide comprises or consists of amino acids 17 to 594 of SEQ ID NO: 2.

In another embodiment, the present invention relates to an isolated polypeptide having dextranase activity encoded by a polynucleotide that hybridizes under high stringency conditions, or very high stringency conditions with (i) the mature polypeptide coding sequence of SEQ ID NO: 1, or (ii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding polypeptides having dextranase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having dextranase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the present invention relates to an isolated polypeptide having dextranase activity encoded by a polynucleotide having a sequence identity to the mature polypeptide coding sequence of SEQ ID NO: 1 of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for dextranase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides having Dextranase Activity

A polypeptide having dextranase activity of the present invention may be obtained from fungi of the genus Acrophialophora. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is an Acrophialophora polypeptide, e.g., a polypeptide obtained from Acrophialophora fusispora, and in particular a polypeptide obtained from Acrophialophora fusispora CBS380.55.

Strains of this species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 25 to 594 of SEQ ID NO: 2 of at least 80%, at least 85%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 25 to 594 of SEQ ID NO: 2.

The catalytic domain preferably comprises or consists of amino acids 25 to 594 of SEQ ID NO: 2 or an allelic variant thereof; or is a fragment thereof having dextranase activity.

In another embodiment, the present invention also relates to catalytic domains encoded by polynucleotides that hybridize under high stringency conditions, or very high stringency conditions (as defined above) with (i) the nucleotides 73 to 1782 of SEQ ID NO: 1, or (ii) the full-length complement of (i) (Sambrook et al., 1989, supra).

In another embodiment, the present invention also relates to catalytic domains encoded by polynucleotides having a sequence identity to nucleotides 73 to 1782 of SEQ ID NO: 1 of at least 80%, at least 85%, at least 90%, at least 95%, at least 96%, at least 97%, at least 98%, at least 99%, or 100%.

In another embodiment, the present invention also relates to catalytic domain variants of amino acids 25 to 594 of SEQ ID NO: 2 comprising a substitution, deletion, and/or insertion at one or more (e.g., several) positions. In one aspect, the number of amino acid substitutions, deletions and/or insertions introduced into the sequence of amino acids 25 to 495 of SEQ ID NO: 2 is 10, e.g., 1, 2, 3, 4, 5, 6, 8, or 9.

Polynucleotides

The present invention also relates to isolated polynucleotides encoding a polypeptide, or a catalytic domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Acrophialophora*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Sac-*

*charomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a Acrophialophora cell. In a more preferred aspect, the cell is a Acrophialophora fusispora cell. In a most preferred aspect, the cell is Acrophialophora fusispora CBS380.55.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Compositions

The present invention in a further embodiment relates to compositions comprising the dextranase according to the invention. Such compositions may further comprise a stabilizer. The stabilizer may in one embodiment be selected from glycerol and trisodium citrate dihydrate.

Uses

In a particular embodiment according to the invention, the dextranase is contemplated for use in the sugar cane industry for removing dextran/reducing viscosity from various sugar solutions.

In one aspect the invention relates to a use of the dextranase of the invention, for reducing viscosity in a sugar solution.

In a further aspect the invention relates to a method for reducing viscosity in a sugar solution comprising contacting the sugar solution with a dextranase according to the invention.

Sugar solution: In the present context a "sugar solution" means any solution comprising sugar derived from either sugar cane or sugar beet. In particular the sugar solution is selected from the group comprising any juice (including primary juice, secondary juice, mixed juice, sulphittated juice, limed juice, decanted juice, filtered juice, evaporated juice, concentrated juice, or juices derived from unit operations of sugarcane Mills, beet sugar mills or sugar refinery), any syrup (concentrated syrup, sulphitated sugar, floated syrup, limed syrup, syrup derived from unit operation of sugarcane mills, sugar beet industry or sugar refinery), any massacuite (massacuite A, massacuite B, massacuite C), any molasses, any magma, raw sugar solution, and/or VHP sugar solution, also affinated sugar, melted sugar, clarified sugar, carbonated sugar, phosphatated sugar, (including any sugar solution derived from unit operation of sugar refinery).

The dextranase may be added at any suitable step during the raw sugar production process. In particular the dextranase may be added to the sugar cane juice before or during clarification. Other suitable points to add dextranase could be to the holding sugar juice tanks or to syrup tanks. In another particular embodiment the dextranase is added during the evaporation step, e.g., to the melasse stream between evaporators, more particularly prior to the last evaporator.

The dextranase according to the invention has a pH activity profile suitable applications in a pH range from 4.0 to 8.0, particularly from 5.0 to 7.0, more particularly from 5.5 to 6.5.

The dextranase according to the invention further has an optimal temperature profile in the range from 30° C. to 65° C. Preferable the dextranase is therefore applied in the methods of the present invention in the range from 30-65° C., particularly from 40-65° C., more particularly from 50-65° C.

The present invention is further described by the following numbered paragraphs.

Paragraph [1]. An isolated polypeptide having dextranase activity, selected from the group consisting of:
(a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
(b) a polypeptide encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i);
(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
(d) a variant of the mature polypeptide of SEQ ID NO: 2 comprising a substitution, deletion, and/or insertion at one or several positions; and
(e) a fragment of the polypeptide of (a), (b), (c), or (d) that has dextranase activity.

Paragraph [2]. The polypeptide of paragraph 1, having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

Paragraph [3]. The polypeptide of paragraph 2, having least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the dextranase activity of the mature polypeptide of SEQ ID NO: 2.

Paragraph [4]. The polypeptide of paragraph 2, having least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the dextranase activity of the mature polypeptide of SEQ ID NO: 2.

Paragraph [5]. The polypeptide of paragraph 2, having least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 90% of the dextranase activity of the mature polypeptide of SEQ ID NO: 2.

Paragraph [6]. The polypeptide of paragraph 2, having least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the dextranase activity of the mature polypeptide of SEQ ID NO: 2.

Paragraph [7]. The polypeptide of paragraph 2, having least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 100% of the dextranase activity of the mature polypeptide of SEQ ID NO: 2.

Paragraph [8]. The polypeptide of paragraph 1, which is encoded by a polynucleotide that hybridizes under high stringency conditions, or very high stringency conditions with (i) the mature polypeptide coding sequence of SEQ ID NO: 1, or (ii) the full-length complement of (i).

Paragraph [9]. The polypeptide of paragraphs 1, which is encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1.

Paragraph [10]. The polypeptide of any of paragraphs 1-9, comprising or consisting of SEQ ID NO: 2 or the mature polypeptide of SEQ ID NO: 2.

Paragraph [11]. The polypeptide of paragraph 10, wherein the mature polypeptide is amino acids 17 to 594 of SEQ ID NO: 2.

Paragraph [12]. The polypeptide of any of paragraphs 1-11, which is a variant of the mature polypeptide of SEQ ID NO: 2 comprising a substitution, deletion, and/or insertion at one or several positions.

Paragraph [13]. The polypeptide of any of paragraphs 1-12, which is a fragment of SEQ ID NO: 2, wherein the fragment has dextranase activity.

Paragraph [14]. A composition comprising the polypeptide of any of paragraphs 1-13 and a stabilizer.

Paragraph [15]. The composition according to paragraph 14, wherein the stabilizer is glycerol.

Paragraph [16]. A use of the dextranase of any of the paragraphs 1-13, for reducing viscosity in a sugar solution.

Paragraph [17]. A method for reducing viscosity in a sugar solution comprising contacting the sugar solution with a dextranase according to any of paragraphs 1-13.

Paragraph [18]. The method according to paragraph 17, wherein the dextranase is added before clarification, in holding juice tanks, before an evaporator step, and/or in syrup tanks.

Paragraph [19]. The method according to any of the paragraphs 17-18, wherein pH is in the range from 4.0 to 8.0, particularly from 5.0 to 7.0, more particularly from 5.5 to 6.5.

Paragraph [20]. The method according to any of the paragraphs 17-19, wherein the temperature is in the range from 30-65° C., particularly from 40-65° C., more particularly from 50-65° C.

Paragraph [21]. An isolated polynucleotide encoding the polypeptide of any of paragraphs 1-13.

Paragraph [22]. A nucleic acid construct or expression vector comprising the polynucleotide of paragraph 21 operably linked to one or more control sequences that direct the production of the polypeptide in an expression host.

Paragraph [23]. A recombinant host cell comprising the polynucleotide of paragraph 21 operably linked to one or more control sequences that direct the production of the polypeptide.

Paragraph [24]. A method of producing a polypeptide having dextranase activity, comprising:
(a) cultivating the host cell of paragraph 23 under conditions conducive for production of the polypeptide; and
(b) recovering the polypeptide.

The present invention is further described by the following examples that should not be construed as limiting the scope of the invention.

EXAMPLES

Strains

*Aspergillus oryzae* MT3568 strain was used for heterologous expression of SEQ ID NO: 2, encoded from SEQ ID NO: 1. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. Protoplasts of *Aspergillus oryzae* MT3568 were prepared according to WO 95/002043.

Strain CBS380.55 (isolated from forest soil in Patharia, India (1955)), *Acrophialophora fusispora*, was used as the source for the DNA encoding the dextranase of SEQ ID NO: 2.

Media and Solutions

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

DAP-4C-1
11 g MgSO4,7H2O
1 g KH2PO4
2 g C6H8O7,H2O
20 g Dextrose
10 g Maltose
5.2 g K3PO4,H2O
0.5 g Yeast Extract
0.5 ml KU6 Trace metal sol.(AMG) (MSA-SUB-FS-0042)
Mix until completely solved
1 ml Dowfax 63N10 was added
Adjust volume with Milli-Q-water up to 1000 ml
CaCO3 tabl. á 0.5 g (add 1 tabl./200 ml)

Before inoculation, each shake flask á 150 ml was added 3.5 ml di-Ammoniumhydrogenphosphat (NH4)2HPO4 50%, and 5.0 ml Lactic acid 20%.

KU6 Trace metal sol.(AMG) (MSA-SUB-FS-0042)
6.8 g $ZnCl_2$
2.5 g $CuSO_4.5H_2O$
0.13 g Nickel Chloride anhydrous
13.9 g $FeSO4.7H_2O$
8.45 g $MnSO_4.H_2O$
3 g $C_6H_8O_7.H_2O$
Ion exchanged water up to 1000 ml

| Raw material | Chem. formula | Supplier | 7-cif. no. | Amount | |
|---|---|---|---|---|---|
| Zinc Chloride | $ZnCl_2$ | Merck | 102-108816 4965 | 6.8 | g |
| Copper Sulfate | $CuSO_4 \cdot 5H_2O$ | Merck | 109-102790 0771 | 2.5 | g |
| Nickel Chloride anhydrous | NiCl2 | Merck | 101-806722 6652 | 0.13 | g |
| Iron Sulfate | $FeSO_4 \cdot 7H_2O$ | Merck | 103965 | 13.9 | g |
| Manganese Sulfate | $MnSO_4 \cdot H_2O$ | Merck | 105941 | 8.45 | g |
| Citric acid | $C_6H_8O_7 \cdot H_2O$ | Merck | 100244 | 3 | g |
| Ion exchanged water up to | | | | 1000 | ml |

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 μl/500 ml) were added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of FeSO$_4$.7H$_2$O, 0.7 g of MnSO$_4$.H$_2$O, 0.8 g of Na$_2$MoO$_4$.2H$_2$O, 10 g of ZnSO$_4$.7H$_2$O, and deionized water to 1 liter.

Example 1

Cloning, Expression and Fermentation of the *Acrophialophora fusispora* Dextranase The gene (SEQ ID NO: 1) encoding the dextranase disclosed herein as SEQ ID NO: 2 was amplified by PCR. The PCR was composed of 1 µl of genomic DNA of the strain CBS380.55 *Acrophialophora fusispora*, 0.75 µl of cloning primer forward (SEQ ID NO: 3) (10 µM), 0.75 µl of primer cloning primer reverse (SEQ ID NO: 4) (10 µM), 3 µl of 5×HF buffer (Finnzymes Oy, Finland), 0.25 µl of 50 mM MgCl$_2$, 0.30 µl of 10 mM dNTP, 0.15 µl of PHUSION® DNA polymerase (Finnzymes Oy, Finland), and 8.8 µl PCR-grade water. The amplification reaction was performed using a Thermal Cycler programmed for 2 minutes at 98° C. followed by 30 cycles each at 98° C. for 15 seconds, 60° C. for 30 seconds, and 72° C. for 1 minutes and 30 seconds; and 3 minutes at 72° C. The amplification reaction was performed using a Thermal Cycler programmed for 2 minutes at 98° C. followed by 35 cycles each at 98° C. for 10 seconds and 72° C. for 1 minute and 30 seconds.

```
Dex5-F
                                              (SEQ ID NO: 3)
5'-ACACAACTGGGGATCCACCATGTTTTCTGTTCTTCTGGGCTGGC-3'

Dex5-R
                                              (SEQ ID NO: 4)
5'-AGATCTCGAGAAGCTTATCAATTAATAGCCCACTGCCCCCA-3'
```

The PCR product was isolated on 1.0% agarose gel electrophoresis using TAE buffer where the PCR band was excised from the gel and purified using a GFX® PCR DNA and Gel Band Purification Kit (GE Healthcare, Hillerød Denmark) according to manufacturer's instructions. DNA corresponding to the *Acrophialophora fusispora* dextranase gene SEQ ID NO: 1 was cloned into the expression vector pDAu109 (WO2005/042735) previously linearized with Bam HI and Hind III, using an IN-FUSION™ Dry-Down PCR Cloning Kit (BD Biosciences, Palo Alto, Calif., USA) according to the manufacturer's instructions.

A 1 µl volume of the undiluted ligation mixture was used to transform BD Phusion-Blue (Clontech). Two colonies were selected on LB agar plates containing 100 µg of ampicillin per ml and cultivated overnight in 2 ml of LB medium supplemented with 100 µg of ampicillin per ml. Plasmid DNA was purified using an Jetquick Plasmid Miniprep Spin Kit (Genomed GmbH, Løhne, Germany) according to the manufacturer's instructions. The *Acrophialophora fusispora* dextranase gene sequence was verified by Sanger sequencing before heterologous expression. One plasmid designated as Dex5-1 (containing SEQ ID NO: 1) was selected for heterologous expression of the dextranase gene in an *Aspergillus oryzae* MT3568 host cell.

*Aspergillus oryzae* MT3568 strain was used for heterologous expression of SEQ ID NO: 1/SEQ ID NO: 2. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. Protoplasts of *Aspergillus oryzae* MT3568 were prepared according to WO 95/002043.

One hundred µl of *Aspergillus oryzae* MT3568 protoplasts were mixed with 1-2 µg of the *Aspergillus* expression vector with the cloned dextranase gene and 250 µl of 60% PEG 4000 (Applichem, Darmstadt, Germany) (polyethylene glycol, molecular weight 4,000), 10 mM CaCl$_2$, and 10 mM Tris-HCl pH 7.5 and gently mixed. After 30 min of incubation at 37° C., 4 ml of topagar (temp. 40° C.) was added, and the protoplasts were spread onto COVE plates for selection. After incubation for 4-7 days at 37° C. spores of four transformants were inoculated into 0.5 ml of DAP-4C-01 medium in 96 deep well plates. After 4-5 days cultivation at 30° C., the culture broths were analyzed by SDS-PAGE to identify the transformants producing the largest amount of recombinant dextranase from CBS380.55 *Acrophialophora fusispora*, and the culture broths were also analyzed in assays for confirmation of activity.

Spores of the best transformant were spread on COVE plates containing 0.01% TRITON® X-100 in order to isolate single colonies. The spreading was repeated twice.

Fermentation for Purification

An *Aspergillus oryzae* transformant constructed as described above was fermented in 150 ml DAP-4C-01 medium in 500 ml fluted shake flasks incubated at 30° C. in a shaking platform incubator rotating at 150 RPM for 5 days and further used for assays as described below.

The enzyme was purified using Anion exchange chromatography using starting buffer A: 20 mM Phosphate pH 6.0 and elution with a 100% gradient of buffer B: same as A with 1M NaCl. The eluted proteins were tested with AZCL-dextran substrate to confirm dextranase activity. The positive fractions were pooled and exchanged into 20 mM Tris Buffer, pH 7.0.

Example 2

Dextranase Activity

The dextranase was successfully purified and the activity confirmed by AZCL-dextran.

Activity was measured by reducing ends at different temperature and pH. Dextran was used in 0.02% because of the background that generates when using reducing ends.

The dextranase according to the invention is active at a wide pH/temperature range, with a maximum at T=62° C. and a pH optimum at 5.5. The temperature profile is shown in FIG. 1.

LC-MS (Liquid Chromatography-mass Spectrometry)

The analysis is performed using an LTQ Deca max IonTrap equipped with an ESI source and an Accela HPLC system with a PDA detector. A BEH Acquity CSH C18 column (2.1×100 mm) is used for the separation at a flow rate of 250 µL/min and 65° C. The gradient is as follows: A: 0.15% HCOOH in water, B: HCOOH in MeCN; 0 min 17% B, 4 min 17% B, 14 min 24.3% B, 15 min 95% B, 16 min 17% B, 20 min 17% B. 5 µL of samples is injected and UV detection is at 245 nm. The spray settings are as follows: Capillary temp 275° C., sheath gas flow 40 l/min and source voltage of 5 kV.

Figure 2:
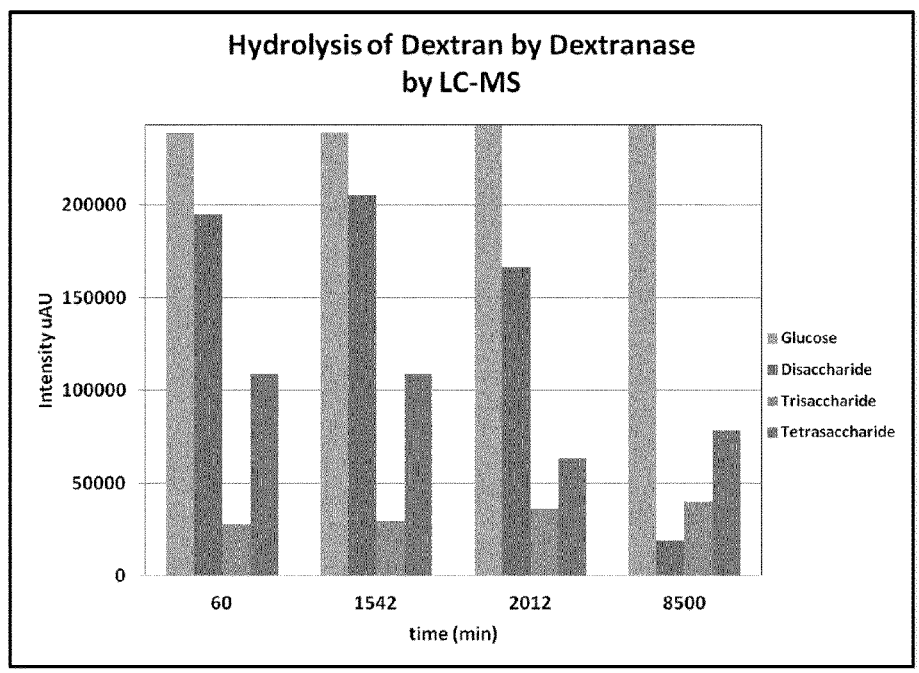
FIG. 2 shows hydrolysis of dextran by dextranase followed by LC-MS. The main products after day 6, correspond to glucose monosaccharide and tetrasaccharide. The glucose intensity reached the detector upper limit after day 1. For each time point in the figure the columns represent (in the same order): glucose, disaccharide, trisaccharide, tetrasaccharide respectively.

The hydrolysis of dextran by dextranase was followed by LC-MS. The reaction mixture was incubated at pH 7 and room temperature; at different time points a sample was removed from the reaction mix and precipitated with EtOH (1:2) for further preparation to LC-MS run. The substrate dextran was 1% in the reaction mix and the enzyme concentration 0.5 mg/mL. The results show that the main products of hydrolysis under these conditions, is glucose monosaccharide followed by tetrasaccharide. The disaccharide is further hydrolyzed in time, while the tetrasaccharide and trisaccharide remain in the same level. The complete hydrolysis is shown in FIG. 2. For each time point in the figure the columns represent (in the same order): glucose, disaccharide, trisaccharide, tetrasaccharide respectively.

Example 3

Reduction in Viscosity in Synthetic Juice Using the Dextranase of the Invention Compared to a Commercial Dextranase Plus L Materials and Methods
Enzymatic Hydrolysis
Samples
  Synthetic juice and synthetic syrup prepared from white sugar collected from Barra Grande Mill (from Zilor group);
  0.25% (w/v) Dextran solution (prepared using Phosphate buffer pH 6.6 and Acetate buffer pH 5.5).
Equipment
  Analytical balances, Thermo-mixers (2-1.5 mL), Micropipettes, Vipr device, Eon Micro-plate Reader
Chemicals
  1M phosphate buffer (pH 6.6 and 7.0), 1M acetate buffer (pH 5.5), Tap water, Dextran from *Leuconostoc* spp (Sigma-Aldrich 09184-250G-F; the measured moisture was 7%);
Enzymes
  Dextranase Plus L (available from Novozymes NS)
  Dextranase from *A. fusispora* (SEQ ID NO: 2)
Hydrolysis was run in triplicate. Preparation of the synthetic syrup: the white sugar was dissolved in phosphate buffer 50 mM (pH 7) achieving a final pH 6.6 and final concentration of 50% w/w. Preparation of synthetic juice: the white sugar was dissolved in phosphate buffer 100 mM (pH 6.6) achieving a final pH 6.5 and final concentration of 15% w/w (or alternatively dissolved in the acetate buffer 100 mM pH 5.5 and final concentration of 15% w/w). All synthetic syrup and juice samples as well as dextran solution (using white sugar sample) were spiked with dextran to result in a final concentrations of 0.5% (w/v) for syrup and 0.25% w/v for juice.

Aliquots were distributed equally in the tubes (final volumes of 1.5 mL). The dose of enzymatic solution used in the case of syrup solution was 166 ppm; in case of juice and dextran solutions, enzymatic solution dose of 16 ppm was applied (see the protein dose in the following). Tubes were incubated at 55° C. while enzymatic products were diluted (1:10 and 1:100) to be added in a dose volume of 2.5 microL. After enzyme addition, tubes were returned to the thermomixer at 55° C. under agitation (~300 rpm) for 20 min for syrup, and 15 min for juice and dextran solutions. The reaction was stopped by incubation in boiling water for 5 min, followed by ice bath. For tubes without dextran, the same volume of water was added to keep all at the same dilution.

Figure 3:
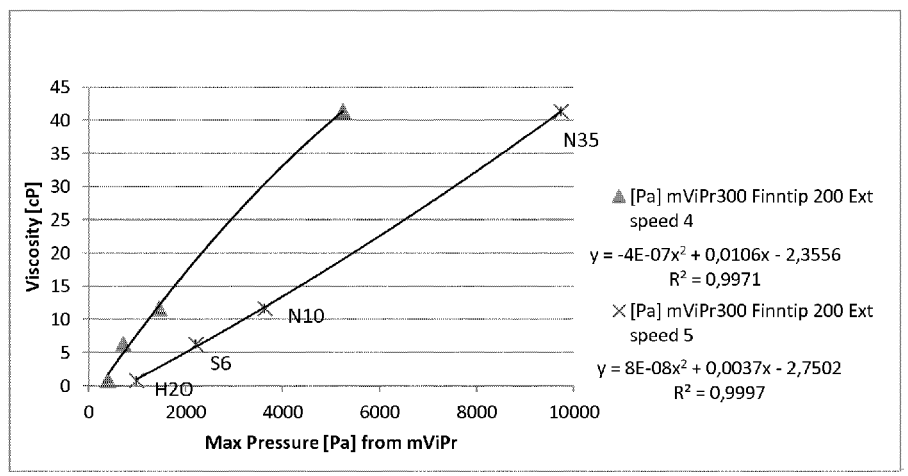
FIG. 3 shows proportionality between the measured pressure and viscosity (calibration curves) using the mViPr pipette. It shows dispensation measurements of pressure in Pascal [Pa] as a function of the actual viscosity [cp] of four viscosity standards (water and S6, N10, N35—Fluka viscosity and density standards) pipetting 200 µL using the 300 µL Finntip Extended tip (model: PMP-105-030J) at speed 4 and 5.

Viscosity Measurement
  Viscosity measurement was performed using Vipr Technology at room temperature using Brand Tips 0-200 uL (speed 3; volume of 200 uL). Viscosity is usually measured by rheological instrument, such as Brookfield viscometer. The viscosity of a solution is a measure of the rate of deformation upon exposure to shear stress (the force required to generate a liquid flow). The ViPr technology is based on the pressure drop needed to generate a liquid flow at constant velocity. This is achieved by measuring the pressure in the headspace of an automated pipette (mViPr) during aspirating and dispensing. Thus this technology provides a method of determining enzyme activity in a fluid, wherein the activity over time provides a viscosity-change in the fluid, by the use of a device equipped with a pressure sensor to determine the change in the fluid viscosity over time as a measure of the enzyme activity. This technology has been described in detail in WO2011/107472. As an example of ViPr technology, the proportionality between the measured pressure and viscosity (calibration curves) using the mViPr pipette is shown in FIG. 3. It corresponds to dispensation measurements in Pascal of four viscosity standards (water and S6, N10, N35—Fluka viscosity and density standards) pipetting 200 μL using the 300 μL Finntip Extended tip (model: PMP-105-030J) at speed 4 and 5. Data is presented as pressure [Pa] as a function of the actual viscosity [cp].

To validate the methodology presented, Table 1 shows values of viscosity of different samples of syrups measured using a Brookfield viscometer and mViPr pipette. Viscosity measurement on Brookfield viscometer (model DV-II) was performed at 30° C., 60 rpm, using spindle 18 and the SSA (Small Sample Adapter) vessel. Vessel was load with 6 mL of sample, and temperature was equilibrated at 30° C. (~5 min) before taking the readings.

TABLE 1

Viscosities of sugarcane (SC) syrup samples using Brookfield viscosimeter and mViPr pipette. mViPr determinations using mViPr300 pipette with a Finn tip 200 Extended tip (PMP-105-030J) and aspirate/dispense speed of 4. Volume = 200 μl ([Coefficient of Variation]$_{average}$ = 0.8%)

| Samples | Viscosity Brookfield (cP) | Viscosity mViPr (cP) |
|---|---|---|
| SC syrup 1 | 10.6 | 10.38 |
| SC syrup 2 | 12.5 | 11.32 |
| SC syrup 3 | 11.3 | 10.19 |
| SC syrup 4 | 11.8 | 10.03 |
| SC syrup 5 | 11.5 | 9.63 |
| SC syrup 6 | 12.2 | 10.57 |

Reducing Sugars Measurement
  Dextranase assay measures the release of reducing sugars from dextran with Ferricyanide reagent (adsorption at 420 nm). Procedure: add 190 microL of each sample to be evaluated into 2 mL centrifuge tubes. Then, add 1.5 mL of ferricyanide reagent (20 g Na2CO3 and 0.4 g potassium ferricyanide dissolved into 1 L volumetric flask). The tubes were incubated for 12 minutes at 96° C. and 300 rpm in a thermomixer (Eppendorf). Cool tubes in flow water and transfer 300 microL of each tube to wells on microplate. Finally, read absorbance at 420 nm (Eon Microplate Reader).

Figure 4:
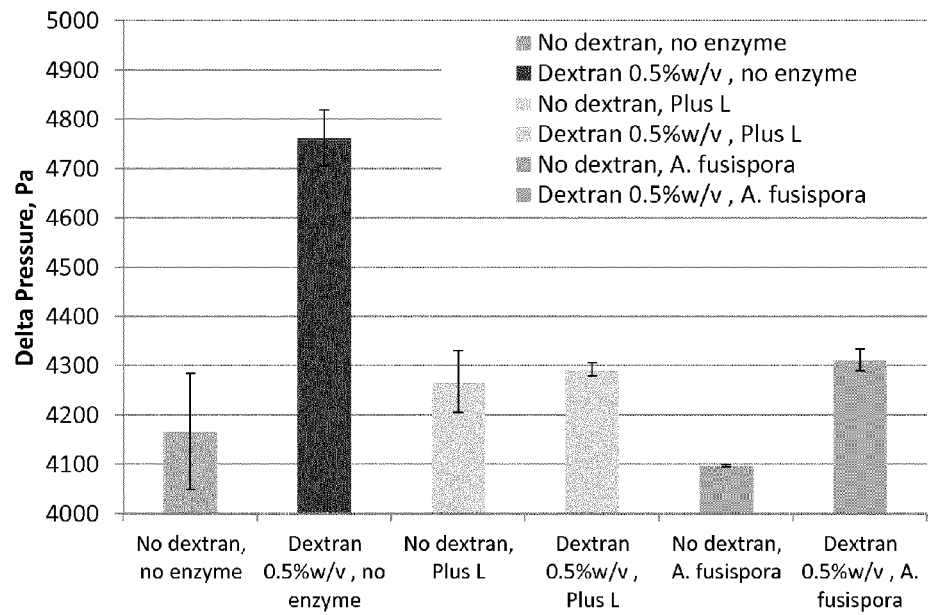
FIG. 4 shows the performance of the two dextranase enzymes, Dextranase Plus L and the dextranase according to the invention, in reducing viscosity on synthetic syrup (50% w/w) enriched with dextran (0.5% w/v). The incubation condition was 55° C. for 20 min. The viscosity was measured by the Vipr technology.

FIG. 4 shows the performance of the two dextranase enzymes in reducing viscosity on synthetic syrup (50% w/w) enriched with dextran (0.5% w/v). The syrup was prepared using a phosphate buffer (pH 7.0) leading to a solution of pH 6.6. The enzyme dose was 1.08 ppm (w/v) for the commercial product (Dextranase Plus L) and 0.25 ppm (w/v) for the *A. fusispora* dextranase (approx. 4-fold lower). The incubation condition was 55° C. for 20 min. The viscosity was measured by the Vipr technology. The Vipr pipette provided pressure measurements during aspirating and dispensing the samples. Parameters for the use of Vipr pipette were speed 3, aspired/dispensed volume of 200 uL and tip used was a Brand 0-200 uL.

The values of pressure shown in FIG. 4 correspond to a Delta Pressure, i.e., the difference between the minimum and maximum pressure for aspiration and dispense for a given sample. These values are proportional to viscosity within a certain dynamic viscosity range which depends on speed and tip diameter. In principle, aspiration and dispense pressures should be equal; however, contribution from gravity results in slightly higher numerical values for aspiration compared to dispense. One important parameter is the set point of the ambient pressure (that must be constant during the whole period of the analysis). Because we verified that a small variation on the set point during the day of the analysis was interfering in obtaining reproductive and comparable measurements, we decided to use the delta Pressure.

Figure 5:
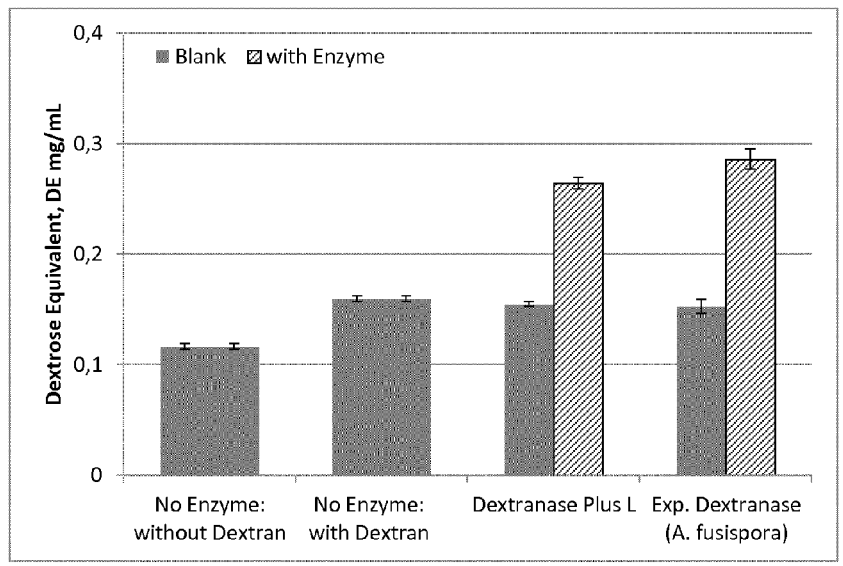
FIG. 5 shows the performance of dextranase enzymes in reducing viscosity on synthetic juice (15% w/w) enriched with dextran (0.25% w/v). Conditions: 55° C.; pH 5.5 (ACETATE buffer); 15 min. Protein dose: 0.025 ppm (w/v). Comparison based on Dextrose Equivalent concept.

FIG. 5 shows the performance of the two dextranase enzymes acting on synthetic juice (15% w/w) enriched with dextran (0.25% w/v). The performance is evaluated by the concept of dextrose equivalent (DE). Note that at this evaluation, the sugar sample was dissolved in 0.1M acetate buffer pH 5.5, which is the pH normally found for this type of substrate in Sugar Mills. All samples are submitted by the treatment under conditions of 55° C.; pH 5.5 (acetate buffer); 15 min. When no enzymes are added to samples (first two bars in FIG. 5), one can see only a very small difference of DE (or absorbance) between the sample enriched with dextran and the one without dextran. Hence, insignificant amount of reducing sugar is derived from the breaking down of dextran due to the methodology applied. In case of samples with enzymes, blanks refer to the sample with addition of the respective denatured enzyme (enzymes are put in boiling water for 5 min, followed by ice bath). A comparison among the blanks and sample with no enzyme confirm the effectiveness of the denaturing process of enzyme. The initial amount of dextran is 0.25% w/w. FIG. 5 shows low DE for blanks and the efficiency of the two dextranase can be compared by the difference found between respective bars. The same amount of protein—0.025 ppm (w/v))—for the application of each enzymatic products (Plus L and *A. fusispora* samples) was added to respective tubes. FIG. 5 shows that, under the same enzyme concentration, the enzyme derived from *A. fusispora* has the highest activity for dextran among the evaluated samples (higher dextrose equivalent measured in the substrate after hydrolysis of 15 minutes at 55° C. and pH 5.5). In terms of dextrose equivalent, which reflects the breaking of high MW dextran molecule in the substrate (i.e., an indirect measure of reducing the viscosity), the enzyme derived from *A. fusispora* shows a performance of 23% higher than that demonstrated by commercial sample Plus L (that means an increase in DE content).

Figure 6:
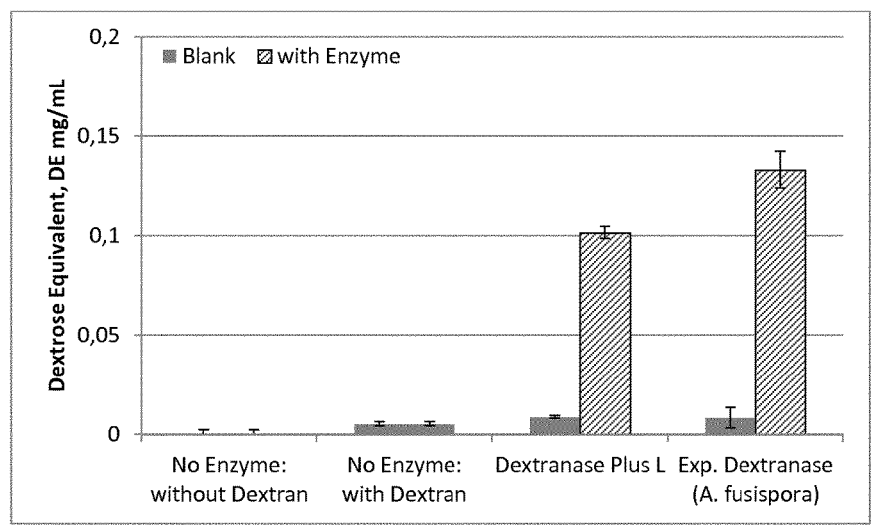
FIG. 6 Performance of dextranase enzymes in breaking down the dextran content on ACETATE buffer solution (pH 5.5) enriched with dextran (0.25% w/v). Conditions: 55° C.; pH 5.5; 15 min. Protein dose: 0.025 ppm (w/v). Comparison based on Dextrose Equivalent concept.

FIG. 6: Performance of dextranase enzymes in breaking down the dextran content on ACETATE buffer solution (pH 5.5) enriched with dextran (0.25% w/v). Conditions: 55° C.; pH 5.5; 15 min. Protein dose: 0.025 ppm (w/v). Comparison based on Dextrose Equivalent concept.

FIG. 6 shows the performance of the two dextranase enzymes acting directly on dextran solution (0.25% w/v) using acetate buffer 0.1M and pH 5.5, which is the pH value usually found for this kind of substrate in Sugar Mills. The performance was evaluated by the concept of dextrose equivalent. Samples were incubated at 55° C.; pH 5.5; 15 min. Again, when no enzymes were added to samples, only a very small difference of DE between the sample enriched with dextran and the one without dextran was observed (i.e., insignificant amount of reducing sugar was derived from breaking down dextran due to the methodology applied on this matrix). A protein dose of 0.025 ppm (w/v) for the application of each enzymatic product (Plus L and *A. fusispora* samples) was used in the assay. One can see from FIG. 6 that, under the same enzyme concentration, the enzyme derived from *A. fusispora* has the highest activity for dextran among the evaluated samples (higher dextrose equivalent measured in the substrate after hydrolysis of 15 minutes at 55° C. and pH 5.5). In terms of dextrose equivalent, the enzyme derived from *A. fusispora* showed a performance of 36% higher than that demonstrated by commercial sample Plus L. This value is higher than the performance found for the case of synthetic juice.

Example 4

Comparative Example of Viscosity Reduction in Synthetic Juice, Sugarcane Syrup, and Synthetic Syrup, Using the Dextranase from *A. fusispora* and a Commercial Dextranase, Dextranase Plus L Performance was tested on synthetic juice (15% w/w), sugarcane syrup (54.8° Brix; collected from a Sugarcane Mill) and synthetic syrup (50% w/w), all enriched with dextran (0.5% w/v).

Enzymatic Hydrolysis

Samples
  Synthetic juice and synthetic syrup prepared from white sugar collected from Sugar Mill 1;
  Syrup collected from Sugar Mill 1;
  0.5% (w/v) Dextran solution.

Equipment
  Analytical balances, Incubators (rotisseries), Micropipettes, Brookfield viscometer (Dv2T LV), Eon Microplate Reader Chemicals
  1M phosphate buffer (pH 6.6), 1M acetate buffer (pH 5.5), Tap water, Dextran from *Leuconostoc* spp (Sigma-Aldrich 09184-250G-F; the measured moisture was 7%);

Enzymes
  Dextranase Plus L (*Sequoia* database: Z4T4Z/U7319; commercial product from NZ);
  Experimental Dextranase from *A. fusispora* (*Sequoia* database: Z4TFB/U76FS);

Experiments of hydrolysis were run in triplicate. Preparation of synthetic syrup: white sugar was dissolved in phosphate buffer 50 mM (pH 6.6) at final concentration of 50% w/w. Preparation of synthetic juice: white sugar was dissolved in acetate buffer 100 mM (pH 5.5) at final concentration of 15% w/w. All synthetic syrup and juice samples were spiked with dextran to result in a final concentrations of 0.5% (w/v).

Aliquots were distributed equally in the tubes (final volumes of 20 mL). In case of syrup, enzyme dose was 166 ppm. In case of juice, enzyme dose of 16 ppm was used. Tubes were incubated at 55° C. while enzymes were diluted to be added in a correct dose. After enzyme addition, tubes were returned to the incubator at 55° C. under agitation (~25 rpm) for 30 min. The reaction was stopped by incubation in boiling water for 5 min, followed by cooling on ice.

For the tubes without dextran, the same volume of water was added to keep all at the same dilution.

Viscosity Measurement: Brookfiled Viscometer.

Viscosity measurement was performed using Brookfiled viscometer DV2TLV, SSA (small sample adapter) at 25° C. (Spindle SC4-18/13R; sample volume: 6.7 mL).

Results:

TABLE 2a

Measured viscosity of synthetic juice (15% w/w) enriched with dextran (0.5% w/v); incubated with dextranase enzymes. Conditions: 55° C.; pH 5.5 (0.1M acetate buffer); 30 min. Viscosity is measured using Brookfield viscometer. Enzyme dose: 16 ppm. Protein content (μg/mL): Plus L = 0.108 μg/mL; A. fusispora = 0.025 μg/mL (note 4-fold lower than commercial).

| Viscosity, cp | Sugar Juice | Dextranase Plus L (0.108 μg/mL) | A. fusispora Enzyme (0.025 μg/mL) |
|---|---|---|---|
| with no Dextran | 1.56 ± 0.03 | 1.62 ± 0.06 | 1.55 ± 0.02 |
| with 0.5% w/v Dextran | 2.22 ± 0.04 | 1.73 ± 0.04 | 2.00 ± 0.03 |

TABLE 2b

Results calculated as % reduction.

| | Dextranase Plus L | A. fusispora Enzyme |
|---|---|---|
| Viscosity reduction, % | 75.3 ± 5.4% | 33.8 ± 3.8% |
| Protein Dose (μg/mL) | 0.108 | 0.025 |

TABLE 3a

Measure viscosity of sugarcane syrup (54.8° Brix; collected from a Sugarcane Mill) enriched with dextran (0.5% w/v); incubated with dextranase enzymes. Conditions: 55° C.; pH 6.6 (0.1M phosphate buffer); 30 min. Viscosity is measured using Brookfield viscometer. Enzyme dose: 166 ppm. Protein content (μg/mL): Plus L = 1.08 μg/mL; A. fusispora = 0.25 μg/mL (note 4-fold lower than commercial)

| Viscosity, cp | Real Syrup | Dextranase Plus L (1.08 μg/mL) | A. fusispora Enzyme (0.25 μg/mL) |
|---|---|---|---|
| with no Dextran | 30.76 ± 0.82 | 30.70 ± 1.03 | 30.72 ± 0.69 |
| with 0.5% w/v Dextran | 43.66 ± 0.51 | 31.30 ± 1.65 | 32.66 ± 1.42 |

TABLE 3b

Results calculated as % reduction.

| | Dextranase Plus L | A. fusispora Enzyme |
|---|---|---|
| Viscosity reduction, % | 95.6 ± 12.8% | 85.1 ± 11.0% |
| Protein Dose (μg/mL) | 1.08 | 0.25 |

TABLE 4a

Measure viscosity profile of synthetic syrup (50° Brix) enriched with dextran (0.5% w/v); incubated with dextranase enzymes. Conditions: 55° C.; pH 6.6 (50 mM phosphate buffer); 30 min. Viscosity is measured using Brookfield viscometer. Enzyme dose: 166 ppm. Protein content (μg/mL): Plus L = 1.08 μg/mL; A. fusispora = 0.25 μg/mL (note 4-fold lower than commercial)

| Viscosity, cp | Sugar Syrup | Dextranase Plus L | A. fusispora Enzyme |
|---|---|---|---|
| with no Dextran | 12.51 ± 0.55 | 12.16 ± 1.07 | 12.57 ± 0.40 |
| with 0.5% w/v Dextran | 18.41 ± 0.31 | 13.53 ± 0.08 | 13.85 ± 0.02 |

TABLE 4b

Results calculated as % reduction.

| | Dextranase Plus L | A. fusispora Enzyme |
|---|---|---|
| Viscosity reduction, % | 81.8 ± 1.3% | 76.5 ± 0.39% |
| Protein Dose (μg/mL) | 1.08 | 0.25 |

Example 5

Comparative Example of Temperature Profiles for Dextranase Enzymes in Viscosity Reduction of Sugarcane Syrup, and Sugar Cane Juice, Using the Dextranase from A. fusispora and a Commercial Dextranase, Dextranase Plus L Performance was tested on sugarcane syrup (48° Brix; collected from a Sugarcane Mill) and sugarcane juice (17.6% w/w), both enriched with dextran (0.5% w/v).

The performance of two dextranases—Dextranase Plus L, and the dextranase from A. fusispora—was investigated for reducing viscosity of real juice and syrup from Sugarcane Mills containing 0.5% w/v dextran. The measurement of viscosity after enzymatic hydrolysis is performed by the Brookfield Viscometer (DV2T-LV). Temperature profiles: 50° C., 60° C., 70° C., 78° C.

Enzymatic Hydrolysis

Samples

Syrup collected from Sugarcane Mill 2—1GBR23 (Syrup)—pH 5.954 and 48.08° Brix

Juice collected from Sugarcane Mill 1 (primary Juice)— pH 5.256 and 17.59° Brix

Equipment

Analytical balances, Centrifuges, Thermostatic Bath with agitation (speed 30), Micropipettes, Brookfield Viscometer (DV2T-LV), vacuum filtration.

Chemicals

Dextran from Leuconostoc spp (Sigma-Aldrich 09184-250G-F)

Enzymes

Dextranase Plus L

Dextranase from A. fusispora

Hydrolysis were run in duplicate. Syrup and juice samples were spiked with dextran to result in final concentrations of 0.5% (w/v). In case of juice, the sample corresponds to the primary juice, and has been filtered using glass filter to eliminate any particulate matter and bagacillo.

Aliquots were distributed equally in the tubes (final volumes of 10 mL). In case of syrup, enzyme dose was 100 ppm Plus L and 424 ppm A. fusispora (this ensure the same protein content in final syrup solution: 0.650 μg/mL syrup; Plus L=6.53 mg/mL product; A. fusispora=1.54 mg/mL product). In case of juice enzyme dose of 10 ppm and 42.4 ppm for Plus L and A. fusispora, respectively, were used. After enzyme addition, tubes were incubated in Thermostatic bath with agitation at different temperatures under agitation (30 min$^{-1}$) for 25 min. The reaction is stopped by incubation in boiling water for 5 min, followed by cooling on ice (at least, 15 min).

For the tubes without dextran, the same volume of water was added to keep all at the same dilution.

Viscosity Measurement

Viscosity measurement was performed using Brookfield Viscometer DV2T-LV, at 25° C., using spindle 18 and the SSA (Small Sample Adapter) vessel. Volume of sample standardized to 6.7 ml.

Results:

TABLE 5a

Viscosity values (performance) of dextranase enzymes in reducing viscosity on sugarcane syrup (48% w/w) enriched with dextran (0.5% w/v), at different temperatures. Condition: pH 6.0; 25 min, agitation 30 min$^{-1}$. Viscosity is measured using Brookfield viscometer. Dose/Protein content: 0.650 µg/mL. Viscosity of the Sugarcane syrup: 11.46 ± 0.51 cp with no Dextran; and 13.56 ± 0.21 cp with 0.5% w/v Dextran.

| Viscosity, cp | 50° C. | 60° C. | 70° C. | 78° C. |
|---|---|---|---|---|
| Dextranase Plus L | 11.56 ± 0.40 | 12.05 ± 0.57 | 12.10 ± 0.06 | 11.53 ± 0.53 |
| A. fusispora enzyme | 11.64 ± 0.30 | 11.73 ± 0.30 | 11.85 ± 0.04 | 12.00 ± 0.25 |

TABLE 5b

Results calculated as % reduction.

| Viscosity reduction, % | Dextranase Plus L | A. fusispora |
|---|---|---|
| 50° C. | 95 ± 19% | 91 ± 14% |
| 60° C. | 72 ± 27% | 87 ± 14% |
| 70° C. | 69 ± 03% | 81 ± 02% |
| 78° C. | 96 ± 25% | 74 ± 12% |

TABLE 6a

Viscosity values (performance) of dextranase enzymes in reducing viscosity on sugarcane juice (17.6% w/w) enriched with dextran (0.5% w/v), at different temperatures. Condition: pH 5.2; 25 min, agitation 30 min$^{-1}$. Viscosity was measured using Brookfield viscometer. Dose/Protein content: 0.065 µg/mL. Viscosity of the Sugarcane juice: 1.645 ± 0.007 cp with no dextran, and 1.915 ± 0.007 cp with 0.5% w/v dextran.

| Viscosity, cp | 50° C. | 60° C. | 70° C. | 78° C. |
|---|---|---|---|---|
| Dextranase Plus L | 1.74 ± 0.01 | 1.74 ± 0.01 | 1.77 ± 0.01 | 1.83 ± 0.01 |
| A. fusispora enzyme | 1.73 ± 0.01 | 1.73 ± 0.01 | 1.76 ± 0.01 | 1.81 ± 0.01 |

TABLE 6b

Results calculated as % reduction

| Temp | Dextranase Plus L | A. fusispora enzyme |
|---|---|---|
| 50° C. | 67 ± 03% | 68 ± 00% |
| 60° C. | 67 ± 03% | 68 ± 00% |
| 70° C. | 54 ± 00% | 55 ± 03% |
| 78° C. | 33 ± 03% | 38 ± 05% |

Example 6

Comparative Kinetic Study of Dextranase Enzymes in Viscosity Reduction of Sugarcane Syrup Using the Dextranase from *A. fusispora* and a Commercial Dextranase, Dextranase Plus L Kinetic studies of dextranase enzymes on sugarcane syrup (61° Brix; collected from a Sugarcane Mill 1) enriched with dextran (1% w/v).

The kinetic performance of two dextranases, Dextranase Plus L and dextranase from *A. fusispora*, was investigated for reducing viscosity of syrup from Sugarcane Mills containing 1% w/v dextran. The measurement of viscosity after enzymatic hydrolysis is performed by the Brookfield Viscometer (DV2T-LV). The temperature of incubation was 55° C.

Enzymatic Hydrolysis

Samples
  Syrup collected from Sugarcane Mill 1—pH 5.6 adjusted to 6.5 and 61° Brix Equipment
  Analytical balances, Centrifuges, Thermostatic Bath with agitation (speed 30), Micropipettes, Brookfield Viscometer (DV2T-LV), vacuum filtration.

Chemicals
  Dextran from *Leuconostoc* spp (Sigma-Aldrich 09184-250G-F)

Enzymes
  Dextranase Plus L
  Dextranase from *A. fusispora*

Experiments of kinetic hydrolysis were carried out at SSA vessel Brookfield Viscometer. Syrup was spiked with dextran to result in a final concentration of 1% (w/v).

A volume of 6.7 mL syrup was added to the SSA and solution temperature was allowed to stabilize at 55° C. (then, initial viscosity of syrup was taken). Then, dextranase enzyme was added and the viscosity reduction was recorded as function of time (at least 22 min incubation time). The protein content in final syrup solution was 0.650 µl/ml syrup for both Plus L and *A. fusispora*. Some agitation was ensured by the rotation of the Brookfield spindle when it allowed the shear rate measurements (about 50 rpm).

For the control samples with and without dextran, the same volume of water was added to keep all at the same dilution.

Viscosity Measurement
  Viscosity measurement was performed using Brookfield Viscometer DV2T-LV, at 55° C., using spindle 18 and the SSA (Small Sample Adapter) vessel. Volume of sample standardized to 6.7 ml.

The experiment was repeated twice.
Result of First Run:

| | Viscosity, cp | | |
|---|---|---|---|
| Time (min) | Dextranase Plus L | A. fusispora Enzyme | Temperature (° C.) |
| 0.00 | 22.42 | 22.26 | 54.9 |
| 1.00 | 21.3 | 20.64 | 54.9 |
| 2.00 | 20.64 | 20.28 | 54.9 |
| 3.00 | 20.58 | 20.16 | 54.9 |
| 4.00 | 20.46 | 20.04 | 54.9 |
| 5.00 | 20.4 | 19.98 | 54.9 |
| 6.00 | 20.34 | 19.92 | 54.9 |
| 7.00 | 20.34 | 19.86 | 54.9 |
| 8.00 | 20.28 | 19.8 | 54.9 |
| 9.00 | 20.28 | 19.8 | 54.9 |
| 10.00 | 20.28 | 19.74 | 54.9 |
| 11.00 | 20.22 | 19.68 | 54.9 |
| 12.00 | 20.22 | 19.62 | 54.9 |
| 13.00 | 20.22 | 19.62 | 54.9 |
| 14.00 | 20.22 | 19.56 | 54.9 |
| 15.00 | 20.16 | 19.56 | 54.9 |
| 16.00 | 20.16 | 19.5 | 54.9 |
| 17.00 | 20.16 | 19.5 | 54.9 |
| 18.00 | 20.16 | 19.44 | 54.9 |
| 19.00 | 20.16 | 19.44 | 54.9 |
| 20.00 | 20.16 | 19.38 | 54.9 |
| 21.00 | 20.16 | 19.38 | 54.9 |
| 22.00 | 20.16 | 19.38 | 54.9 |
| end | 19.38 | 19.02 | 55.0 |

Result of Second Run:

| Time (min) | Viscosity, cp | | Temperature (° C.) |
|---|---|---|---|
| | Dextranase Plus L | A. fusispora enzyme | |
| 0.00 | 22.32 | 22.36 | |
| 1.00 | 20.76 | 20.82 | 54.8 |
| 2.00 | 20.52 | 19.68 | 54.8 |
| 3.00 | 20.46 | 19.5 | 54.8 |
| 4.00 | 20.34 | 19.44 | 54.9 |
| 5.00 | 20.22 | 19.38 | 54.9 |
| 6.00 | 20.16 | 19.32 | 54.9 |
| 7.00 | 20.1 | 19.2 | 54.8 |
| 8.00 | 20.04 | 19.14 | 54.8 |
| 9.00 | 20.04 | 19.08 | 54.8 |
| 10.00 | 19.98 | 19.02 | 54.9 |
| 11.00 | 19.98 | 18.96 | 54.9 |
| 12.00 | 19.92 | 18.96 | 54.9 |
| 13.00 | 19.8 | 18.96 | 55.0 |
| 14.00 | 19.74 | 18.96 | 55.0 |
| 15.00 | 19.74 | 18.96 | 55.0 |
| 16.00 | 19.68 | 18.9 | 54.9 |
| 17.00 | 19.68 | 18.9 | 54.9 |
| 18.00 | 19.68 | 18.9 | 54.9 |
| 19.00 | 19.68 | 18.9 | 54.9 |
| 20.00 | 19.68 | 18.9 | 54.8 |
| 21.00 | 19.68 | 18.84 | 54.9 |
| 22.00 | 19.68 | 18.84 | 54.9 |
| end | 19.02 | 18.84 | 54.9 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for reducing viscosity in a sugar solution comprising contacting the sugar solution with an isolated polypeptide having dextranase activity, wherein the amino acid sequence of the polypeptide has at least 92% sequence identity to the sequence of amino acids 17 to 594 of SEQ ID NO: 2.

2. The method of claim 1, wherein the amino acid sequence of the polypeptide has at least 95% sequence identity to the sequence of amino acids 17 to 594 of SEQ ID NO: 2.

3. The method of claim 1, wherein the amino acid sequence of the polypeptide has at least 97% sequence identity to the sequence of amino acids 17 to 594 of SEQ ID NO: 2.

4. The method of claim 1, wherein the amino acid sequence of the polypeptide has at least 98% sequence identity to the sequence of amino acids 17 to 594 of SEQ ID NO: 2.

5. The method of claim 1, wherein the polypeptide comprises the amino acid sequence of amino acids 17 to 594 of SEQ ID NO: 2.

6. The method of claim 1, wherein the polypeptide is a fragment of the amino acid sequence of amino acids 17 to 594 of SEQ ID NO: 2, wherein the fragment has dextranase activity.

7. The method of claim 1, wherein the polypeptide is contacted with the sugar solution before a clarification step, before an evaporator step, in holding juice tanks, and/or in syrup tanks.

8. A recombinant microbial host cell comprising a polynucleotide encoding a polypeptide having dextranase activity, wherein the polynucleotide is operably linked to one or more heterologous control sequences that direct the production of the polypeptide in the host cell and wherein the amino acid sequence of the polypeptide has at least 92% sequence identity to the sequence of amino acids 17 to 594 of SEQ ID NO: 2.

9. The recombinant host cell of claim 8, wherein the amino acid sequence of the polypeptide has at least 95% sequence identity to the sequence of amino acids 17 to 594 of SEQ ID NO: 2.

10. The recombinant host cell of claim 8, wherein the amino acid sequence of the polypeptide has at least 97% sequence identity to the sequence of amino acids 17 to 594 of SEQ ID NO: 2.

11. The recombinant host cell of claim 8, wherein the amino acid sequence of the polypeptide has at least 98% sequence identity to the sequence of amino acids 17 to 594 of SEQ ID NO: 2.

12. The recombinant host cell of claim 8, wherein the polypeptide comprises the amino acid sequence of amino acids 17 to 594 of SEQ ID NO: 2.

13. The recombinant host cell of claim 8, wherein the polypeptide is a fragment of the amino acid sequence of amino acids 17 to 594 of SEQ ID NO: 2, wherein the fragment has dextranase activity.

14. A method of producing a polypeptide having dextranase activity, comprising:
(a) cultivating the host cell of claim 8 under conditions conducive for production of the polypeptide; and
(b) recovering the polypeptide.

15. A method of producing a polypeptide having dextranase activity, comprising:
(a) cultivating the host cell of claim 9 under conditions conducive for production of the polypeptide; and
(b) recovering the polypeptide.

16. A method of producing a polypeptide having dextranase activity, comprising:
(a) cultivating the host cell of claim 10 under conditions conducive for production of the polypeptide; and
(b) recovering the polypeptide.

17. A method of producing a polypeptide having dextranase activity, comprising:
(a) cultivating the host cell of claim 11 under conditions conducive for production of the polypeptide; and
(b) recovering the polypeptide.

18. A method of producing a polypeptide having dextranase activity, comprising:
(a) cultivating the host cell of claim 12 under conditions conducive for production of the polypeptide; and
(b) recovering the polypeptide.

19. A method of producing a polypeptide having dextranase activity, comprising:
(a) cultivating the host cell of claim 13 under conditions conducive for production of the polypeptide; and
(b) recovering the polypeptide.

20. The method of claim 14, wherein the host cell is a filamentous fungal host cell.

* * * * *